US005649550A

United States Patent [19]
Crook

[11] Patent Number: 5,649,550
[45] Date of Patent: Jul. 22, 1997

[54] SURGICAL RETRACTOR LINER AND INTEGRAL DRAPE ASSEMBLY

[75] Inventor: Berwyn M. Crook, Yardley, Pa.

[73] Assignee: Medical Creative Technologies, Inc., Colmar, Pa.

[21] Appl. No.: 606,606

[22] Filed: Feb. 26, 1996

[51] Int. Cl.$^6$ ............................................. A61B 19/00
[52] U.S. Cl. ............................................ 128/849; 128/853
[58] Field of Search ............................... 128/846, 849, 128/856; 602/42, 43, 50, 60, 63, 75, 901

[56] References Cited

U.S. PATENT DOCUMENTS

| | | | |
|---|---|---|---|
| 1,196,250 | 8/1916 | Kuhn | 128/850 |
| 2,305,289 | 12/1942 | Coburg . | |
| 3,332,417 | 7/1967 | Blanford | 128/850 |
| 3,347,226 | 10/1967 | Harrower . | |
| 3,347,227 | 10/1967 | Harrower . | |
| 3,397,692 | 8/1968 | Creager | 128/850 |
| 3,476,109 | 11/1969 | Hurney | 602/63 |
| 4,043,328 | 8/1977 | Cawood | 128/850 |
| 4,188,945 | 2/1980 | Wenander . | |
| 4,926,851 | 5/1990 | Bulley | 602/63 |
| 5,263,922 | 11/1993 | Sova et al. . | |
| 5,366,478 | 11/1994 | Brinkerhoff . | |

*Primary Examiner*—Michael A. Brown
*Attorney, Agent, or Firm*—Howson and Howson

[57] ABSTRACT

A surgical retractor liner and integral drape assembly suitable for inserting in an incision and adjusting in place to prevent cross-contamination during surgery between the incise cavity and the surrounding skin of the patient. A flexible liner impervious to microorganisms has resilient inner and outer rings at either end for holding the liner firmly in the incision. A skirt sealingly joined at the outer ring tapers outwardly and sealingly joins to a drape around a central aperture therein. The inner ring is inserted and expanded against the inner edge of the incision, and the outer ring is rolled down over the liner and skirt to draw the liner taut in the incision and to retract the sides of the incision while positively anchoring the drape in place around the area of the incision.

19 Claims, 2 Drawing Sheets

1

SURGICAL RETRACTOR LINER AND INTEGRAL DRAPE ASSEMBLY

FIELD OF THE INVENTION

The present invention relates generally to improvements in surgical devices, and more particularly to an improved adjustable incision retractor liner and integral drape assembly for preventing cross contamination during surgery between an incision and the external surface area around the incision.

BACKGROUND OF THE INVENTION

The sides of an open incision, as well as matter such as body parts and fluids passing through the incision during surgery, are inherently susceptible to cross-contamination by infectious microorganisms or like matter. Therefore, extreme care is required to insure that any exposed fluids or tissues are completely isolated from each other.

Various designs have been proposed and utilized to prevent transmission of indigenous and exogenous contaminants to healthy viscera from infectious tissues or fluids. U.S. patent application Ser. No. 08/489,044 by Berwyn M. Crook, filed Jun. 9, 1995, now U.S. Pat. No. 5,524,644, describes an incision liner and retractor device which can be installed in an incision, incrementally adjusted in place to form-fit a wide range of cavity wall thicknesses, and retract the sides of the incision apart for better access to the abdominal cavity. It employs a flexible impermeable sleeve with opposite ends terminating at inner and outer resilient O-rings. The inner O-ring is inserted in the cavity by squeezing it through the incision and allowing it to expand around the inner edge of the incision. The outer O-ring is then rolled down over the portion of the liner extending out of the incision until it is tight against the outer rim of the incision and the remaining portion is drawn taut and contiguous with the incision sides. The outer O-ring is generally oblong in cross-section to provide a positive gripping surface for the fingers to roll the outer O-ring more easily, especially when the liner or the surgeon's gloves are slippery.

In many instances, a surgical drape may be first placed over the patient's body before the incision liner and retractor device is installed. This combination further reduces the risk of cross-contamination between the open cavity and the skin around the incision, especially if an organ is brought outside the abdominal cavity to perform surgery on it. However, since the liner and drape are not integrally connected, there is no assurance that the drape may not slide from beneath the outer O-ring and leave the patient's skin exposed in a most vulnerable region immediately adjacent to the incision.

Some prior art surgical protectors address this problem to a limited degree. For instance, U.S. Pat. No. 3,397,692 to Creager, Jr. et al. discloses an incised wound protector in which a resilient ring cemented around the rim of a central aperture in a drape is squeezed together and expanded in the cavity to grip the incised edge of the peritoneum. The drape is bunched together where it passes through the incision and then spreads out over the body surface in radially diminishing wrinkles. U.S. Pat. No. 4,188,945 to Wenander similarly provides a surgical cloth with a semi-rigid thread hemmed in around a central aperture. A portion of the cloth around the aperture is gathered together and inserted in an incision, and then enlarged under the incision edge by increasing the length of thread around the aperture. Like the wound protector of Creager, Jr. et al., a wrinkled surface is created in the incision and around the operating site. Consequently, neither device provides a relatively smooth surface in the incision and around the wound where extracted viscera may be placed nor positive retraction of the sides of the incision. In addition, there is no means for preventing external portions of the drape from slipping in and out of the incision with movement of the surgeon's hand.

OBJECTS OF THE INVENTION

Accordingly, it is an object of the present invention to provide an improved surgical liner and integral drape assembly which prevents exposure to cross-contamination by infectious fluids and solids between an incised cavity and the skin around the incision.

Another object of the invention is to provide a surgical liner and drape assembly which interfaces smoothly and contiguously with the sides of an incision and with the skin around the incision.

Still another object of the invention is to provide an incision liner with integral drape which can be easily installed and adjusted in place to fit a wide range of cavity wall thicknesses, and which will positively insulate an incision and surrounding skin from exposure to indigenous and exogenous contaminants and positively retract the sides of the incision for a wider opening to the cavity.

SUMMARY OF THE INVENTION

These and other objects and aspects of the invention are accomplished with a surgical retractor liner and integral drape assembly which can be inserted in an incision and incrementally adjusted tightly in place in the cavity wall and on the surrounding skin to prevent cross-contamination with body fluids and solids during surgery. It includes a flexible liner impervious to microorganisms with opposite ends terminating at inner and outer resilient O-rings. The inner O-ring is installed in the incision by squeezing opposite sides together, inserting it through the incision and allowing it to expand around the inner edge of the incision. The length of the liner is selected to allow a portion to extend out of the incision for rolling down until it is tight against the outer edge of the incision and retracts the sides of the incision for widening the opening. A skirt fixed at one end around the outer O-ring, and coaxial with the liner, tapers outwardly toward the inner O-ring with the other end sealingly joining the rim of a centrally located aperture in a flexible drape. The extended length of the skirt is at least as long as the portion of the liner fully extending out of the incision when the inner O-ring is expanded against the inner edge. This assures that the drape completely adheres to the surface around the incision and remains fixed in place by the liner and by adhesive patches fixed to the drape. The size of the drape is sufficient to cover the area around the operating site and to prevent it from exposure to any contaminating fluids and tissue.

BRIEF DESCRIPTION OF THE DRAWINGS

The foregoing and other objects, features, and advantages of the invention will become more apparent from the following description of the preferred embodiments when taken in conjunction with the accompanying drawings wherein.

DESCRIPTION OF THE PREFERRED EMBODIMENTS

Figure 1:
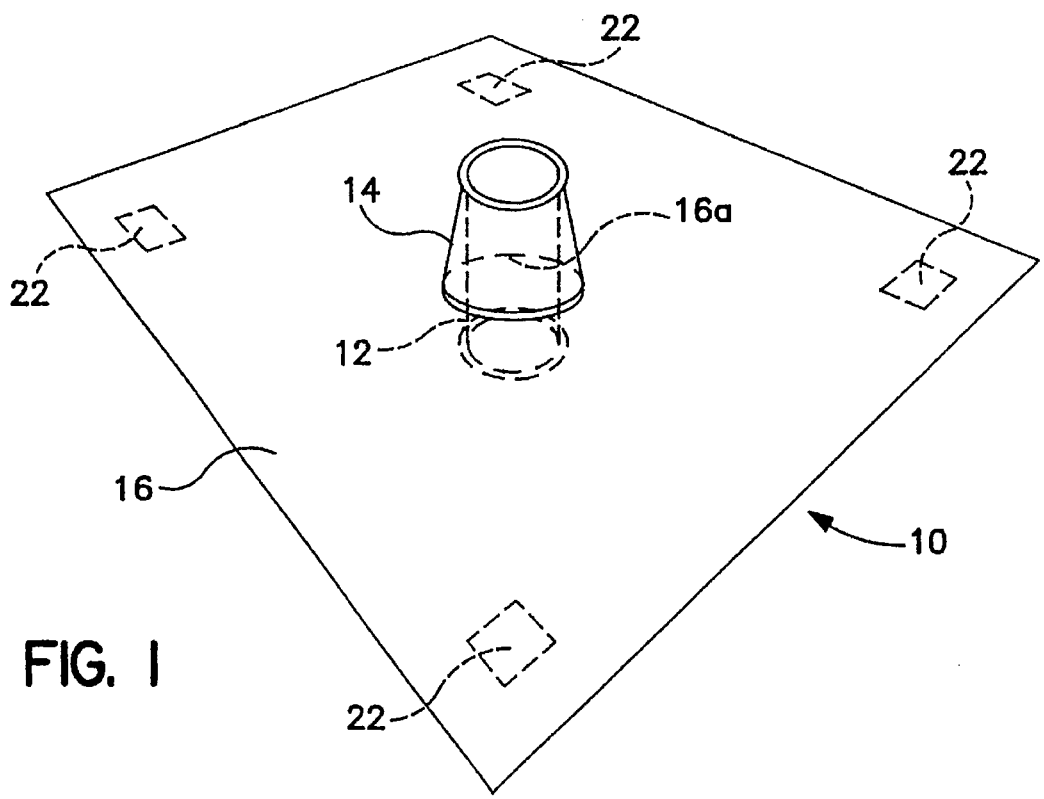
FIG. 1 represents a perspective top view of a surgical retractor liner and integral drape assembly according to the invention.

Referring now to the drawings wherein like reference characters designate like or corresponding parts throughout the several views, there is shown in FIG. 1 a surgical liner and integral drape assembly 10 comprising an incision liner 12 of uniform circumference along its length coaxially extending through a skirt 14 and a central aperture 16a in a drape 16.

Figure 2:
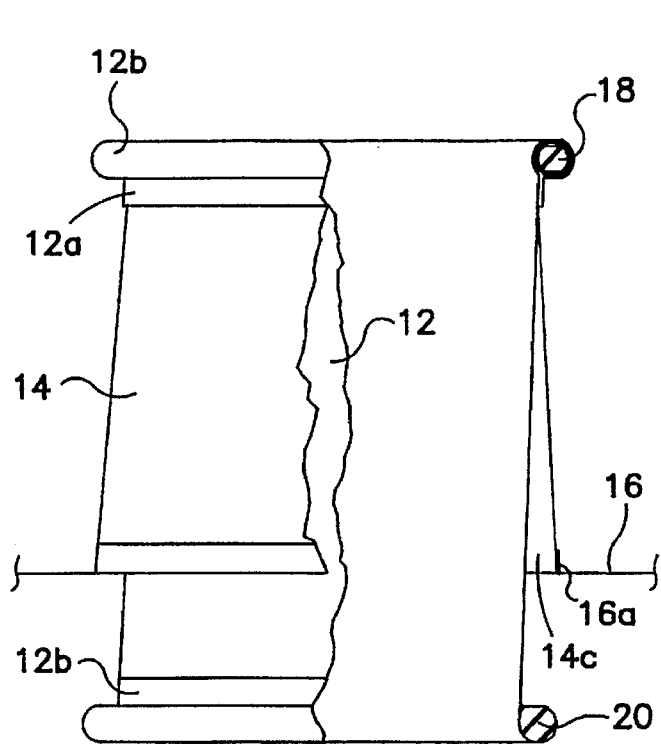
FIG. 2 is a side view partially in cross-section of a portion of the assembly of FIG. 1.
Figure 3:
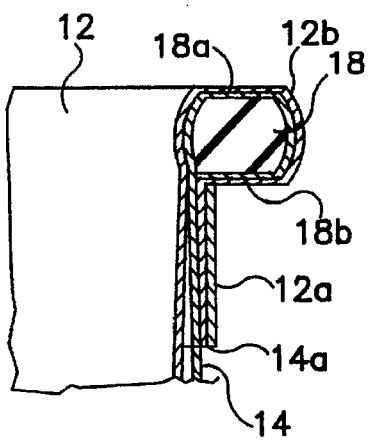
FIG. 3 is an enlargement in cross section of an upper portion of the assembly shown in FIGS. 1 and 2.

As best seen in FIG. 2, liner 12 and skirt 14 have adjacent upper ends which wrap around an outer O-ring 18 and overlap at annular edges 12a and 14a (FIG. 3) and seal to each other and to the outer side skirt 14. A lower end portion of liner 12 wraps around an inner O-ring 20 and overlaps at an annular edge 12b and seals to the outer side of liner 12; whereas a lower end of skirt 14 is sealed around the perimeter of aperture 16a. Liner 12 is essentially uniform in circumference along a central longitudinal axis defined by the extended length of the liner. Skirt 14 is coaxial with liner 12 and tapers outwardly to aperture 16a.

Outer O-ring 18 is generally oblate in cross-section with opposed upper and lower flat chordal sides 18a and 18b substantially normal to the extended length of liner 12. Sides 18a and 18b are located equidistant from and on opposite sides of the centroid of the radial cross-section through O-ring 18. The oblate shape provides an over-center snap action when O-ring 18 is rolled about itself onto liner 12 and skirt 14 for incrementally shortening the upper ends and for resisting unrolling after being shortened.

Inner O-ring 20 is entirely circular in cross-section, but may have a similar cross-section as O-ring 20 for incrementally shortening the lower end of liner 12.

Figure 4:
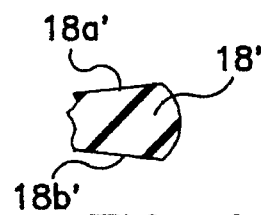
FIG. 4 is a view in radial cross section of an alternate embodiment of an O-ring for use in the upper portion of the assembly shown in FIG. 3.

FIG. 4 illustrates in radial cross-section an alternate embodiment of an outer O-ring 18'. The upper and lower sides 18a' and 18b' taper outwardly from opposite sides of a plane normal to the extended length of liner 12 thereby allowing O-ring 18' to be turned with less resistance around its annular axis due to the lesser mass near the inner circumference O-ring 18'. This structure is particularly desirable for large diameter rings having relatively large diameter cross-sections.

The materials for making assembly 10 are selected to insure stability when installed. Preferred materials, both manufactured by the Dow Chemical Company, are a heat sealable three-mil polyolethin plastic, such as Saranex™ film 2050 for liner 12, and a backing layer for skirt 14 and drape 16. O-rings 20 and 22 are preferably preformed of an elastomeric medical-grade urethane of sufficient hardness to retain the rings expanded in place around the inner and outer rims of the incision. The material must be compliant enough to allow the fingers to turn the outer O-ring 18 over 180° around its annular axis from the preformed configuration. They may be color-coded with different colors, such as white and blue, for easier recognition of the correct O-ring to be inserted in an incision.

Drape 16 may be adhered directly to the skin of the patient or to an underlying drape by an adhesive spread over the underside of the drape, or by adhesive patches 22 at selected locations on the underside of the drape. The size of drape 16 is selected to provide effective protection from exposure to infectious fluids and tissue in the vicinity of the incision.

The length of a fully extended liner 12 is typically around 150 mm to accommodate most wall thicknesses at the incision. An assortment of liner and O-ring diameters are provided to accommodate different lengths of incisions, and the personal preference of the surgeon. Patent application Ser. No. 08/489,044 supra, now U.S. Pat. No. 5,524,044, discloses a table of liner and O-ring diameters available for different incision lengths, and its disclosure is incorporated by reference herein. The urethane O-rings are typically in the range of 50–90 Shore A durometers.

The diameter of an upper length of skirt 14, in a relaxed state before stretching around O-ring 18 and sealing it at edge 14a, corresponds substantially to the diameter of liner 12. The remaining lower portion tapers outwardly to the diameter of aperture 16a which is slightly larger than the diameter of liner 12 to allow clearance for liner 12 to be stretched into contact with the outer rim of the incision. The length of skirt 14 must not be shorter than liner 12 by an amount greater than the thickness of the wall at the incision. If the difference were greater, the drape will not adhere completely to the skin immediately adjacent to the incision. Of course, if the difference is less than the wall thickness, the lower end of skirt 14 will merely bunch up around the uninserted portion of liner 12 and roll onto O-ring 18 but still provide a satisfactory seal. Typically, the thickness of abdominal walls ranges between 25 mm and 75 mm. Therefore, for an overall liner length of 150 mm, an effective skirt length should not be shorter by more than 25 mm, namely an overall length of 135 mm.

Figure 5A:
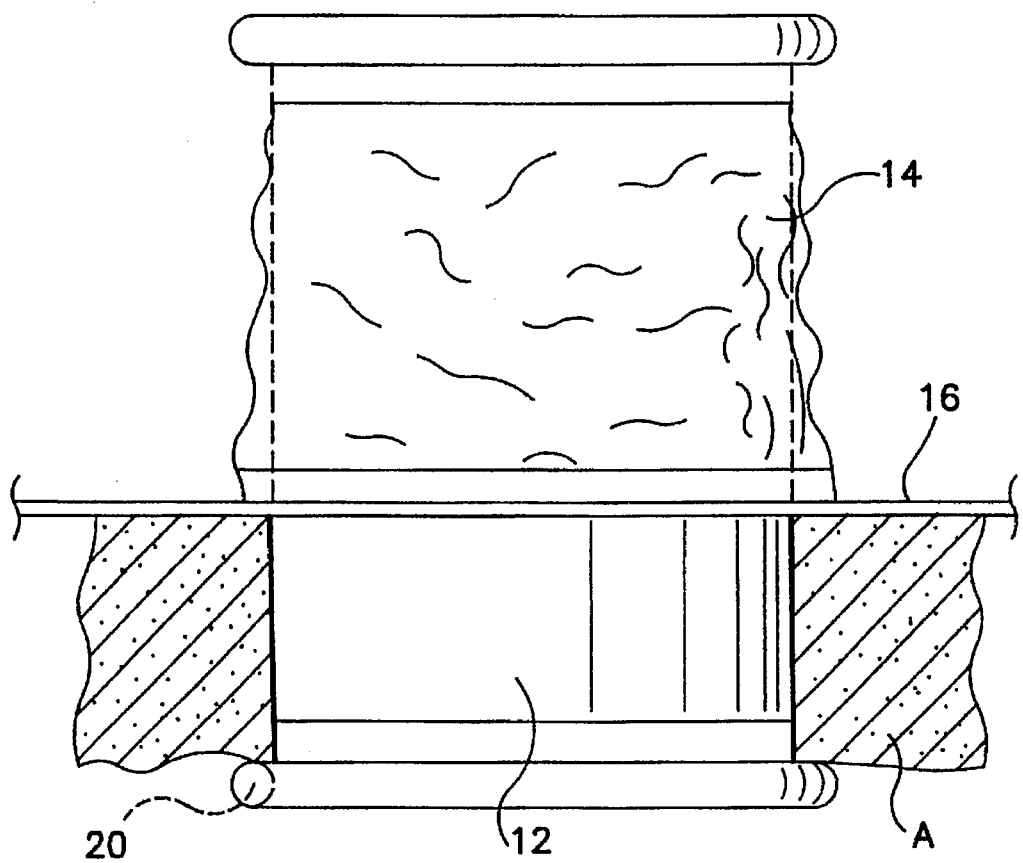
FIGS. 5A and 5B are schematic illustrations of the assembly in two stages of installation in an incision.
Figure 5B:
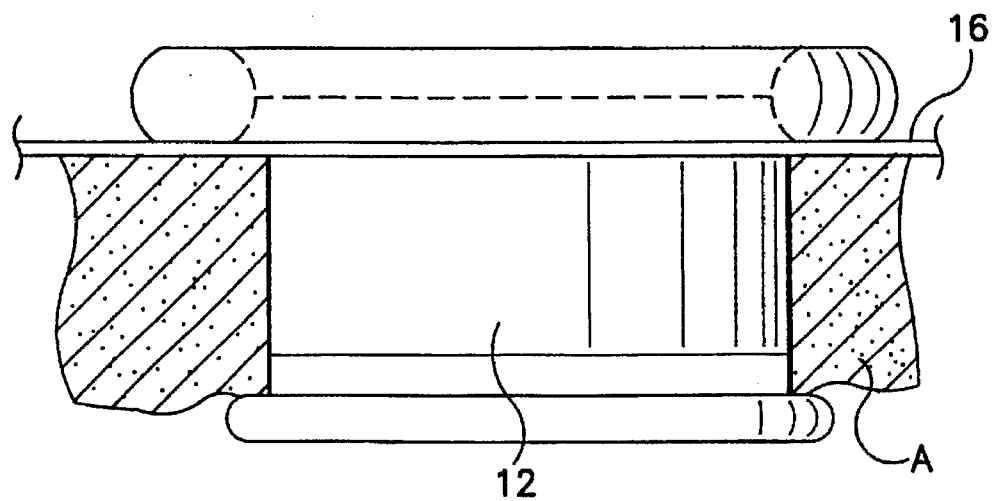

A typical installation of the retractor liner and integral drape assembly 10 is illustrated in two stages in FIGS. 5A and 5B. In FIG. 5a, liner 12 is inserted into an incision in the abdominal wall A with the inner O-ring 20 expanded against the inner rim of the incision and drape 16 adhered to the skin, or to an underlying drape not shown. In this installation skirt 14 is shorter than liner 12 by a difference slightly less than the thickness of the abdomen wall, thereby causing skirt 14 to bunch up around fully extended liner 12. In FIG. 5B, the upper end of the assembly containing O-ring 18 is rolled down over the outside of skirt 14, abuts the top of drape 16 with skirt 12 drawn taut against the incision, and retracts the sides of the incision to widen the opening. Drape 16 is thusly positively anchored against slipping out from under the rolled down portions of liner 12 and skirt 14.

Some of the many advantages and novel features of the invention should now be readily apparent. For example, the invention provides an improved liner and drape assembly which prevents exposure between an incised cavity and the skin around the incision to cross-contamination by infectious fluids and tissue. The assembly is positively anchored in place around the operating site by the installed liner, smoothly interfaces against the sides of the incision and the surrounding skin, and retracts the sides of the incision for a wider opening. It can be easily installed in an incision and adjusted in place to fit a wide range of cavity wall thicknesses as well as provide positive insulation of an incision and surrounding skin from indigenous and exogenous contaminants.

Of course, it will be understood that various changes in the details, materials, steps and arrangement of parts, which have been herein described and illustrated in order to explain the nature of the invention, may be made by those skilled in the art within the principle and scope of the invention as expressed in the appended claims.

I claim:

1. A liner and integral drape assembly for preventing cross-contamination during surgery of infectious fluids and solids between an incision and the external surface around the incision comprising:

a tubular liner of flexible material open at opposed ends thereof;

a continuous skirt of flexible material having opposed first and second ends, said first end sealingly secured around one of said liner ends and coaxial with said liner in their fully extended positions;

a first resilient ring secured around the other one of said liner ends deformable into an oblong shape for insertion with a portion of said liner into the incision and expansion against the inner edge of the incision;

a second resilient ring secured around said one liner end and said first skirt end for rolling adjacent portions of said skirt and said liner on themselves and against the outer edge of the incision; and a drape of flexible material having a central aperture sealingly secured around said second skirt end, the length of said skirt being sufficient for said drape to adhere to the external surface immediately adjacent to the incision.

2. An assembly according to claim 1 wherein said skirt is shorter than said liner in the extended positions.

3. An assembly according to claim 1 wherein said length of said liner exceeds the length of said skirt by less than about 25 mm.

4. An assembly according to claim 1 wherein the length of said liner exceeds the length of said skirt by an amount in the range of about 25 mm and 75 mm.

5. An assembly according to claim 1 wherein said liner is of uniform circumference along the extended length, and said skirt tapers outwardly along the extended length from said first skirt end.

6. An assembly according to claim 1 wherein said liner is made of a sheet of about 3-mil polyolethin plastic.

7. An assembly according to claim 1 wherein said skirt and said drape are made of a backing about 3-mil plastic sheet.

8. An assembly according to claim 1 further comprising:

adhesive patches disposed on one side of said drape for adhering to a patient's skin or an underlying surgical drape.

9. An assembly according to claim 1 wherein said second resilient ring has substantially flat surfaces on opposite sides for enabling tactile gripping and rolling adjacent portions of said liner and said skirt onto said second resilient ring in predetermined increments to shorten said liner and to resist subsequent lengthening thereof.

10. An assembly according to claim 9 wherein said second resilient ring surfaces are transverse to the extended length of said liner and equidistant from the centroid of a radial cross-section thereof.

11. An assembly according to claim 9 wherein said second resilient ring surfaces taper outwardly from a plane transverse to the extended length of said liner.

12. A surgical retractor liner comprising:

a tubular liner open at each of opposed ends thereof, said liner being made of a pliable material impervious to solid and fluid contaminants for inserting lengthwise in a wound;

a continuous skirt of flexible material having opposed first and second ends, said first end sealingly secured around one of said liner ends and coaxial with said liner in their fully extended positions;

an inner O-ring secured around the other one of said liner ends, said inner O-ring having a preformed resilient configuration for overlapping the inner edge of the wound and for squeezing into an oblong shape insertable with a lengthwise portion of the liner adjacent to said inner O-ring in the wound; and an outer O-ring secured around said one liner end and said first skirt end, said outer O-ring having surface means formed integral therewith for overlapping the outer edge of the wound and for rolling adjacent portions of said skirt and said liner lengthwise on themselves about the outer O-ring to shorten the liner in predetermined increments;

said inner and outer rings cooperating with said flexible liner when installed in an incision both to protect the edges of the incision from contamination and to retract the edges from one another to facilitate surgery through the incision, whereby the liner length can be adjusted before or after placement in the wound.

13. An assembly according to claim 12 wherein said skirt is shorter than said liner in the extended positions.

14. An assembly according to claim 12 wherein said length of said liner does not exceed the length of said skirt by more than about 25 mm.

15. An assembly according to claim 12 wherein the length of said liner exceeds the length of said skirt by an amount in the range of about 25 mm and 75 mm.

16. An assembly according to claim 12 wherein: said surface means on said outer O-ring includes opposed flat surfaces enabling tactile gripping and rolling of said skirt and said liner onto said outer O-ring.

17. An assembly according to claim 16 wherein: said opposed surfaces lie in parallel planes perpendicular to a lengthwise extension of said liner to provide said outer O-ring with an oblate cross-section.

18. An assembly according to claim 16 wherein said second ring surfaces taper outwardly from a plane transverse to the extended length of said liner.

19. A liner and drape assembly incrementally adjustable lengthwise for use in surgery comprising:

an elongate flexible liner open at opposite ends;

a flexible skirt open at opposite ends, an inner ring secured to one of said liner ends;

an outer ring secured around one of said skirt ends and around the other one of said liner ends, said outer ring having an oblate transverse cross-section defined by a diametrically opposed pair of arcuate surfaces interconnected by an opposed pair of chordal surfaces;

a flexible drape having a central aperture secured around the other one of said skirt ends, the extended length of said skirt being sufficient for said drape to adhere the skin next to the incision; and said inner and outer rings cooperating with said flexible liner when installed in an incision both to protect the edges of the incision from contamination and to retract the edges from one another to facilitate surgery through the incision.

* * * * *